(12) United States Patent
Zhang et al.

(10) Patent No.: US 10,368,411 B2
(45) Date of Patent: Jul. 30, 2019

(54) ULTRAVIOLET LIGHT MODULE HAVING OUTPUT POWER CONTROL MECHANISM

(71) Applicant: Bolb Inc., San Jose, CA (US)

(72) Inventors: Jianping Zhang, Arcadia, CA (US); Ling Zhou, Dublin, CA (US); Ying Gao, Fremont, CA (US)

(73) Assignee: BOLB Inc., Livermore, CA (US)

( * ) Notice: Subject to any disclaimer, the term of this patent is extended or adjusted under 35 U.S.C. 154(b) by 0 days.

(21) Appl. No.: 15/270,595

(22) Filed: Sep. 20, 2016

(65) Prior Publication Data

US 2018/0084617 A1    Mar. 22, 2018

(51) Int. Cl.

| | |
|---|---|
| F21V 5/04 | (2006.01) |
| H05B 33/08 | (2006.01) |
| G01J 1/42 | (2006.01) |
| F21V 23/04 | (2006.01) |
| A01G 7/04 | (2006.01) |
| A61N 5/00 | (2006.01) |
| A61N 5/06 | (2006.01) |
| A61B 18/00 | (2006.01) |

(52) U.S. Cl.
CPC ......... *H05B 33/0851* (2013.01); *A01G 7/045* (2013.01); *A61N 5/00* (2013.01); *A61N 5/06* (2013.01); *A61N 5/0616* (2013.01); *F21V 5/04* (2013.01); *F21V 23/0457* (2013.01); *G01J 1/429* (2013.01); *A61B 2018/00452* (2013.01); *A61N 2005/0651* (2013.01); *A61N 2005/0661* (2013.01); *G01J 2001/4247* (2013.01); *Y02P 60/149* (2015.11)

(58) Field of Classification Search
CPC .. F21V 29/70; H05B 33/0842; F21Y 2101/02
USPC ......... 315/34, 51, 151, 200 R; 362/268, 331, 362/554, 574
See application file for complete search history.

(56) References Cited

U.S. PATENT DOCUMENTS

| | | | |
|---|---|---|---|
| 3,748,480 A | 7/1973 | Coleman | |
| 3,952,265 A | 4/1976 | Hunsperger | |
| 4,125,777 A | 11/1978 | O'Brien et al. | |
| 5,448,077 A | 9/1995 | Krause | |
| 7,399,091 B2 * | 7/2008 | Lockett | F21V 1/00 |
| | | | 353/120 |
| 8,604,412 B2 * | 12/2013 | Shibayama | G01J 3/02 |
| | | | 250/226 |
| 2003/0116773 A1 * | 6/2003 | Kraus | H01L 31/12 |
| | | | 257/88 |
| 2006/0062508 A1 * | 3/2006 | Guo | C12Q 1/6825 |
| | | | 385/12 |
| 2007/0278512 A1 * | 12/2007 | Loh | B29C 45/1671 |
| | | | 257/99 |

(Continued)

*Primary Examiner* — Wei (Victor) Chan
(74) *Attorney, Agent, or Firm* — Patent Office of Dr. Chung Park (57) ABSTRACT

The invention relates to UV light modules that generate UV light. The UV light module includes: a substrate; a light source mounted on a top surface of the substrate, the light source generates output light; a detector mounted on the top surface of the substrate, the detector detects light incident thereon; and a lens disposed over the light source and the detector. The lens includes a surface on which a portion of the output light is internally reflected and the portion of the output light travels through the lens to the detector.

8 Claims, 5 Drawing Sheets

(56) References Cited

U.S. PATENT DOCUMENTS

| | | | |
|---|---|---|---|
| 2009/0040755 A1* | 2/2009 | Kopp | H05B 33/0869 362/231 |
| 2009/0278034 A1* | 11/2009 | Ackermann | H01L 25/167 250/227.11 |
| 2010/0102199 A1* | 4/2010 | Negley | F21V 7/0008 250/201.1 |
| 2010/0277059 A1* | 11/2010 | Rains, Jr. | B82Y 30/00 313/502 |
| 2010/0289427 A1* | 11/2010 | Walter | B82Y 20/00 315/291 |
| 2011/0254554 A1* | 10/2011 | Harbers | H05B 33/0893 324/414 |
| 2011/0279015 A1* | 11/2011 | Negley | H05B 33/0857 313/501 |
| 2011/0285526 A1* | 11/2011 | Tanaka | H05B 33/0884 340/514 |
| 2012/0155116 A1* | 6/2012 | Gardner | G02B 6/002 362/609 |
| 2013/0257266 A1* | 10/2013 | Ishizaki | H01L 33/504 313/503 |
| 2015/0029742 A1* | 1/2015 | Chen | F21K 9/52 362/555 |
| 2015/0236227 A1* | 8/2015 | Yan | H01L 33/58 257/88 |
| 2016/0161326 A1* | 6/2016 | Chang | G01H 9/00 250/227.14 |

\* cited by examiner

ULTRAVIOLET LIGHT MODULE HAVING OUTPUT POWER CONTROL MECHANISM

BACKGROUND

Technical Field

The present invention relates to lighting devices, and more particularly, to ultraviolet light modules having output power control mechanisms.

Background of the Invention

UV light sources, such as UV light emitting diodes (LEDs), have been used in various applications, such as industrial and cosmetic curing, sterilization of harmful bacteria, indoor gardening, and treatment of human skin condition, so on. For example, AlGaN LEDs emitting at wavelengths in the range of 240-365 nm can be used as ultraviolet light panel backlight sources for germicidal and medical applications. In this case, the input power to the light source must be controlled so that the intensity of the light from the light source is maintained at the target level to ensure sterilization of the germs.

In general, controlling a UV light source is difficult since human cannot directly perceive the UV light. The lens of the human eye blocks most of the light in the wavelength range of 300-400 nm and shorter wavelengths are blocked by the cornea. Since human cannot directly perceive the UV light, visual inspection of the output light cannot determine whether the UV light source is properly working or not. Thus, to monitor the operational status of the UV light source, an indicator that generates a signal which can be perceived by a human operator, such as visible light or sound, is needed.

The indicator may include a detector, such as photodiode, that generates photocurrent in response to the UV light incident thereon, where a feedback mechanism may use the photocurrent to control the intensity of light from the UV light source. For instance, the input power to the UV light source may be increased if the photocurrent decreases below the target level. However, the conventional feedback mechanisms have a few problems. First, the spectral responsivity of a conventional photodiode decreases as the wavelength decreases. The spectral responsivity may be defined as a ratio of the generated photocurrent to incident light power. Since the UV light is in the short wavelength range, the conventional UV detector has low responsivity. Thus, there is a need for a waveguide mechanism that can direct a portion of the light from the light source to the detector so that the detector can receive sufficient amount of light during operation. Second, the intensity of the light emitted by a conventional UV light source is very low. In addition, the UV light is absorbed by the air, causing the intensity of light incident on a UV detector to decrease rapidly as the optical path length between the UV light source and detector increases. As such, there is a need for an arrangement of the detector and light source so that the loss of light during transmission from the light source to the detector is minimized. With these being said, it is preferred that the detector detects (wastes) as small amount of UV light power as possible, to maximize the UV light output power for application purposes.

SUMMARY OF THE DISCLOSURE

In one aspect of the present invention, an apparatus for generating light includes: a substrate; a light source mounted on a top surface of the substrate, the light source generates output light; a detector mounted on the top surface of the substrate, the detector detects light incident thereon; and a lens disposed over the light source and the detector. The lens includes a surface on which a portion of the output light is internally reflected and the portion of the output light travels through the lens to the detector.

In another aspect of the present invention, an apparatus for generating light includes: a substrate; a light source mounted on a top surface of the substrate, the light source generates output light; a detector mounted on the top surface of the substrate, the detector detects light incident thereon; and a lens disposed over the light source and the detector wherein the light source, detector, and lens are arranged such that a total of 1-10% of the light output power from the light source is transmitted via the lens to the detector, to generate a measurable photocurrent in the detector which can be used as a feedback to control the light source's output power.

In another aspect of the present invention, an apparatus for generating light includes: a substrate; a light source mounted on a top surface of the substrate, the light source generates output light; a detector mounted on the top surface of the substrate, the detector detects light incident thereon; and a waveguide having a first end disposed over the light source and a second end disposed over the detector. A portion of the output light enters the waveguide through the first end, travels through the waveguide by internal reflection and exits the waveguide through the second end to the detector.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Figure 1:
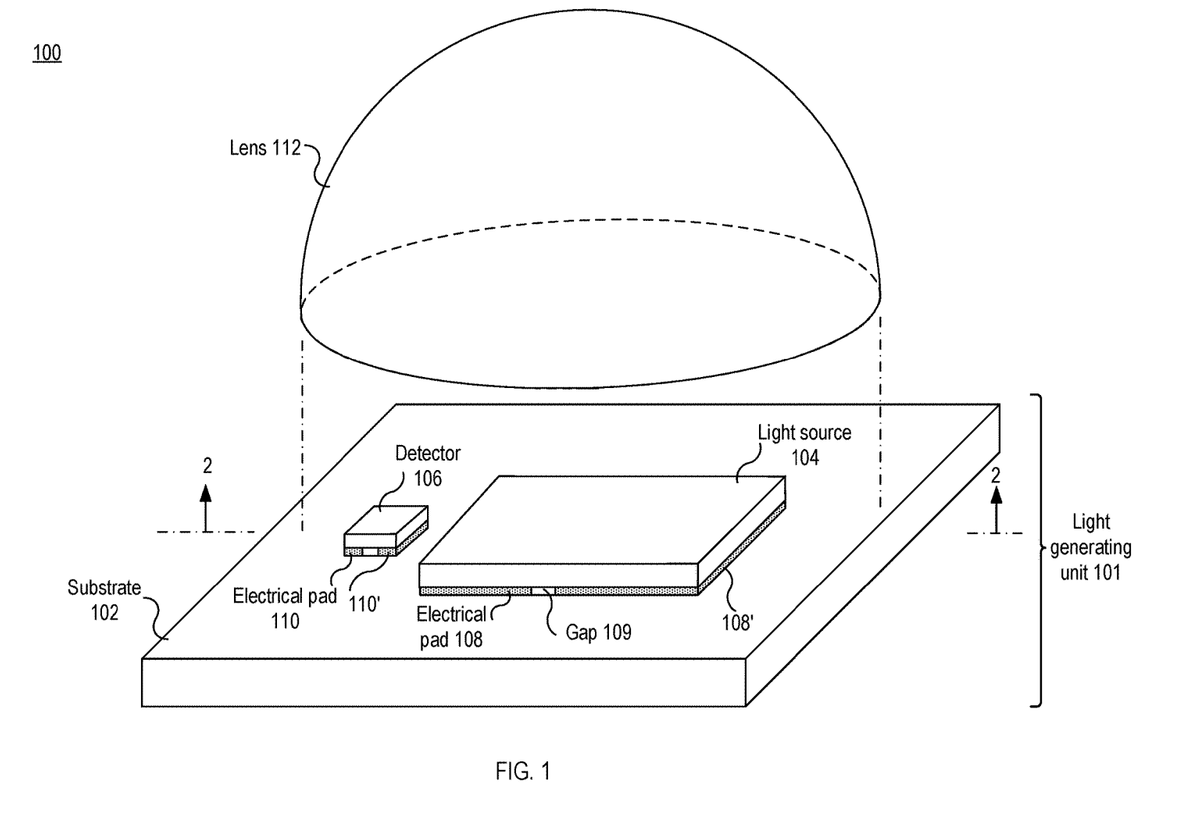
FIG. 1 shows an exploded perspective view of a UV light module according to embodiments of the present invention.
Figure 2:
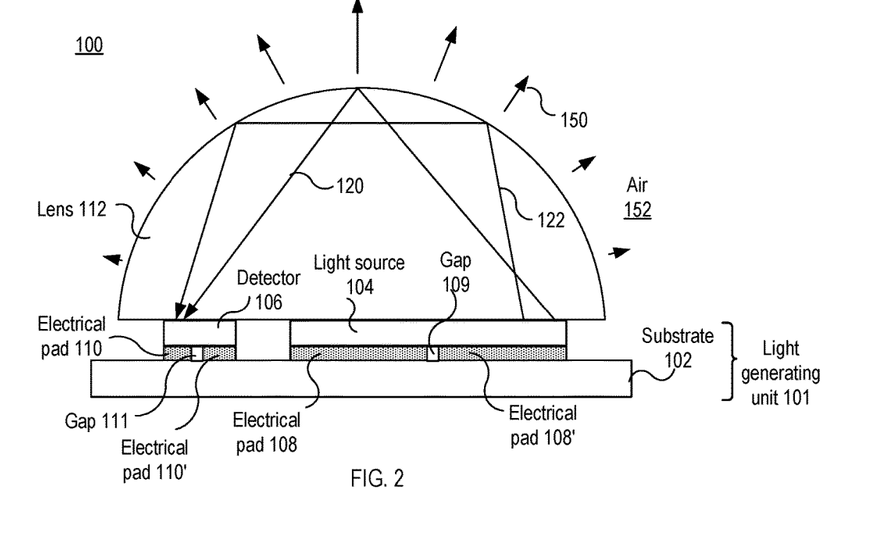
FIG. 2 shows a cross sectional view of the UV light module in FIG. 1, taken along the direction 2-2.

FIG. 1 shows an exploded perspective view of a UV light module 100 according to embodiments of the present invention. FIG. 2 shows a cross sectional view of the UV light module in FIG. 1, taken along the direction 2-2. As depicted, the UV light module 100 may include: a light generating unit 101; and a lens 112 disposed over the light generating unit. The light generating unit 101 may include: a substrate 102 for physically supporting and wiring electrical components mounted thereon; a UV light source (or shortly light source) 104 secured to the substrate 102 by electrical pads 108 and 108'; and a UV detector (or, shortly detector) 106 secured to the substrate 102 by electrical pads 110.

In embodiments, the substrate 102 may be a printed circuit board (PCB) and include conductive tracks, pads, or other features etched from copper sheets laminated onto an electrically non-conductive substrate, such as glass epoxy. The substrate 102 may be single sided (one copper layer), double sided (two copper layers) or multi-layer (such as bottom, middle, top layers) and conductors on different layers may be connected with vias. It is noted that other suitable material, such as ceramic, may be used for the substrate 102.

In embodiments, the light source 104 may be a light emitting diode (LED) that includes layers stacked on a substrate. For instance, the stacked layers may include a buffer layer formed on a sapphire substrate, an n-contact layer coupled to an n-pad/electrode, an n-clad layer, an active layer, a p-clad layer, and a p-contact layer coupled to a p-pad/electrode, and generate UV light when electrical current is applied through the n-pad and p-pad. In embodiments, the light source 104 may be an AlGaN multiple-quantum-well (MQW) LED with emission wavelengths in the range of 205-365 nm, optionally in the range of 240-280 nm for solar blind applications.

In embodiments, the two electrical pads 108 and 108' may be formed of electrically conducting material, such as Au or AuSn, and electrically coupled to the p-pad/electrode and n-pad/electrode of the light source 104, respectively. In embodiments, to secure the light source 104 to the substrate 102, the electrical pads 108 and 108' may be formed on the top surface of the substrate 102 and then the light source 104 may be positioned on the electrical pads 108 and 108'. Subsequently, the electrical pads 108 and 108' may be heated and cured so that the electrical pads 108 and 108' can securely bond the light source 104 to the substrate 102.

The substrate 102 may communicate electrical signals, including the input current (or input power) to the light source, with the light source 104 via the electrical pads 108 and 108'. The gap 109 may electrically separate the electrical pads 108 and 108' from each other and, optionally, may be filled with electrically insulating material.

In embodiments, the detector 106 may be a photodiode that generates electrical current, photocurrent, in response to the UV light incident thereon. In embodiments, the detector 106 may have a light absorbing intrinsic semiconductor layer sandwiched by an n-type and a p-type semiconductor layers forming a so called PIN structure and include a pair of anode and cathode. For instance, the detector 106 may have layers stacked on a sapphire substrate, where the stacked layers may include an n-type epitaxial layer coupled to a first electrode, an active layer (intrinsic layer) for converting UV light into photocurrent, and a p-type epitaxial layer coupled to a second electrode, where the photocurrent flows in the detector 106 from the first electrode to the second electrode. In embodiments, the detector 106 may be an AlGaN PIN photodetector detecting UV light, optionally in the solar blind UV range of 240-280 nm.

In embodiments, the two electrical pads 110 and 110' may be formed of electrically conducting material, such as Au or AuSn, and electrically coupled to the first and second electrodes of the detector 106, respectively. The detector 106 may be mounted on the substrate 102 in the similar manner as the light source 104. In embodiments, the electrical pads 110 and 110' may be formed on the top surface of the substrate 102 and then the detector 106 may be positioned on the electrical pads 110 and 110'. Subsequently, the electrical pads 110 and 110' may be heated and cured so that the electrical pads 110 can securely bond the detector 106 to the substrate 102.

The substrate 102 may communicate electrical signals, including the output photocurrent from the detector 106, with the detector 106 via the electrical pads 110 and 110'. The gap 111 may electrically separate the electrical pads 110 and 110' from each other and, optionally, may be filled with electrically insulating material.

In embodiments, the output light of the light source 104 may have a substantially uniform intensity distribution over the top surface of the light source 104. To narrow down the output light to a specific angular range or to steer the output light to a specific direction, the lens 112 may be mounted on the light source 104. In embodiments, the light 150 steered by the lens 112 may have the Lambertian distribution, having peak intensity in the direction normal to the top surface of the light source 104.

In embodiments, the lens 112 may extract most of the output light from the light source 104 and internally reflect only a small portion of the output light to the detector 106. In embodiments, the lens 112 may reflect about 1-10% of the output light from the light source 104 to the detector 106. For the purpose of illustration, it is assumed that the responsivity of the detector 106 is 0.16 A/W and the detector 106 receives 10% of the output light from the light source 104. If the output power of the light source 104 is 10 mW, the detector 106 may generate the photocurrent of 160 µA (=10 mW×10%×0.16 A/W). Likewise, if the output power of the light source 104 is 100 mW and the lens 112 reflects about 1% of the output light from the light source 104, the same detector 106 may generate the photocurrent of 160 µA (=100 mW×1%×0.16 A/W). In some other embodiments, where photo detectors of larger responsivity are used as the detector 106, the amount of light output power coupled through the lens 112 to the detector 106 can be even less than 1% of the total light output power from the light source 104. For example, a phototransistor type of photodetector can have responsivity larger than 100 A/W, even larger than 1000 A/W, even larger than 10000 A/W. In such cases, the light power coupled through the lens 112 to the detector 106 can be greatly less than 1% of the total light output power from the light source 104, to give a measurable photocurrent in the detector 106. A measureable current means the current is larger than 1 pA for very sophisticated current measurement instrument, or larger than 1 nm for less sophisticated current measurement instrument, or larger than 1 μA for simple current measurement instrument. For portable applications, it is preferred that the photocurrent generated by the detector 106 is larger than 1 μA.

The lens 112 may be formed of material that is transparent to the UV light emitted by the light source 104. In embodiments, the lens material may be quartz, sapphire or aluminum nitride (AlN). Since the index of refraction of the lens material is higher than the air 152, a portion of the light from the light source 104 may be internally reflected on the interface between the lens 112 and the air 152, as indicated by the arrows 120 and 122, and transmitted toward the detector 104 through the lens 112. As depicted, the lens 112 may be disposed over the detector 106 so that the reflected beam is guided to the detector 106 through the lens 112. Unlike in the conventional systems where the UV light is transmitted through the air, in embodiment, the UV light is transmitted through the optically transparent material (i.e., the lens 112), reducing the loss of light during its travel to the detector 106. Also, as the detector 106 is disposed in close proximity to the light source 104, the optical path between the light source 104 and detector 106 is minimized, further reducing the loss of light during its travel from the light source to the detector.

It is noted that lens 112 may not only steer the output light from the light source 104 but also increase the efficiency of the light source 104. In general, the index of refraction of the semiconductor material for the light source 104 is very high, while the index of refraction of the air is about 1.0. Thus, without the lens 112, a large portion of the output light from the semiconductor material is internally reflected back on the interface between the semiconductor material and the air, reducing the efficiency of the light source 104. In contrast, lens 112, of which the index of refraction ranges from 1.45-2.25, would reduce the internal reflection at the interface between the semiconductor and the lens, thereby enhancing the efficiency of the light source 104.

In embodiments, the lens 112 may be secured to the light source 104 and detector 106 by the Van Der Waal's forces. To achieve the attractive Van Der Waal's forces between the light source 104 (and detector 106) and the lens 112, the bottom surface of the lens 112 and the top surface of the light source 104 (and detector 106) may be polished so that the air gap between the lens 112 and the light source 104 (and detector 106) is removed when the lens 112 is firmly pressed against the light source 104 and detector 106 during assembly of the UV light module 100.

As depicted in FIGS. 1 and 2, the lens 112 may have a shape of a spherical dome, and preferably a hemisphere. In FIG. 1, the substrate 102, light source 104 and detector 106 are shown to have rectangular shapes when they are seen from the top. However, it should be apparent to those of ordinary skill in the art that other suitable geometrical shapes, such as circle, oval, and hexagon, may be used in place of the rectangles.

Figure 3:
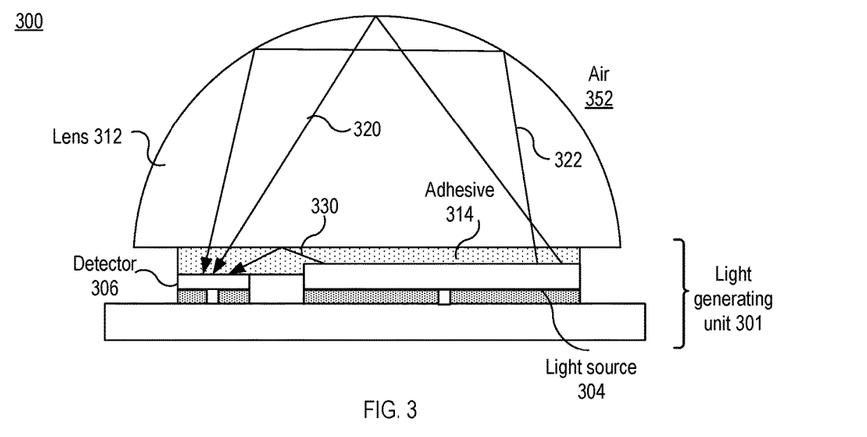
FIG. 3 shows a UV light module according to embodiments of the present invention.

FIG. 3 shows a UV light module 300 according to embodiments of the present invention. As depicted, the UV light module 300 is similar to the UV light module 100, with the difference that an adhesive layer 314 is disposed between the lens 312 and the light generating unit 301. More specifically, the adhesive layer 314, which may be formed of epoxy or resin and transparent to the UV light emitted by the light source 304, may be used to secure the lens 312 to the light source 304 and detector 306. In embodiments, the index of refraction of the adhesive layer 314 may be 1.4-1.7

In embodiments, the lens 312 may extract most of the light that is transmitted through the adhesive layer 314. Also, as in the UV light module 100, a small portion (about 1-10%) of the light may be internally reflected on the interface between the lens 312 and the air 352 and transmitted to the detector 306 through the lens 312, as indicated by the arrows 320 and 322. In addition, a portion of the output light from the light source 304 may be internally reflected on the interface between the adhesive layer 314 and the lens 312 and transmitted through the adhesive layer 314 to the detector 306, as indicated by the arrow 330. As such, the adhesive layer 314 may not only bond the lens 312 to the light generating unit 301 but also provide an additional waveguide for transmitting a portion of the light from the light source 304 to the detector 306 therethrough.

As discussed above, in the UV light module 100, the lens 112 may be attached to the light source 104 (and detector 106) by the Van Der Waal's forces. Thus, it is necessary that the light source 104 and detector 106 have the same height in the direction normal to the top surface of the substrate 102. Also, the bottom surface of the lens 112 and the top surfaces of the light source 104 and detector 106 need to be polished. In contrast, in the UV light module 300, the lens 112 may be bonded to the light source 304 and detector 306 by the adhesive layer 314. Thus, in the UV light module 300, it may not be necessary to polish the surfaces of the lens 312, light source 304 and detector 306. Also, as depicted in FIG. 3, it may not be necessary that the light source 304 and detector 306 have the same height.

Figure 4:
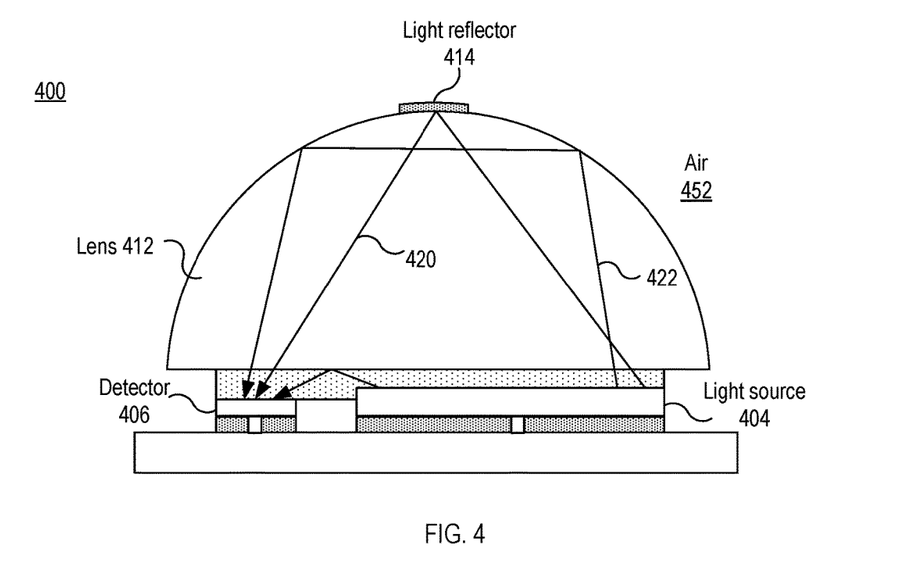
FIG. 4 shows a UV light module according to embodiments of the present invention.

FIG. 4 shows a UV light module 400 according to embodiments of the present invention. As depicted, the UV light module 400 is similar to the UV light module 300, with the difference that a light reflector 414 is formed on the top surface of the lens 412. In embodiments, the light reflector 414 may increase the reflection of light on the interface between the lens 412 and the air 452 to thereby increase the amount of light transmitted to the detector 406.

In embodiments, the light reflector 414 may be formed of light reflecting material, such as aluminum, silver or distributed Bragg reflector (DBR), deposited on the top surface of the lens 412. Since the light reflector 414 may increase the reflectance on the interface between the lens 412 and the air 452, the light reflector 414 may increase the intensity of light incident on the detector 406. In embodiments, the light reflector 414 may refer to a portion of the top surface of the lens 412, where the portion has a higher surface roughness than the rest. Since the surface roughness may increase the amount of light diffused at the interface between the lens 412 and the air 452, the light reflector 414 may increase the intensity of light incident on the detector 406.

In FIG. 4, the light reflector 414 is located near the center of the lens 412. However, it should be apparent to those of ordinary skill in the art that the light reflector 414 may be disposed at any other suitable location on the top surface of the lens 412. Also, it should be apparent to those of ordinary skill in the art that the size of the light reflector 414 may vary depending on the amount of light to be reflected thereby.

Figure 5:
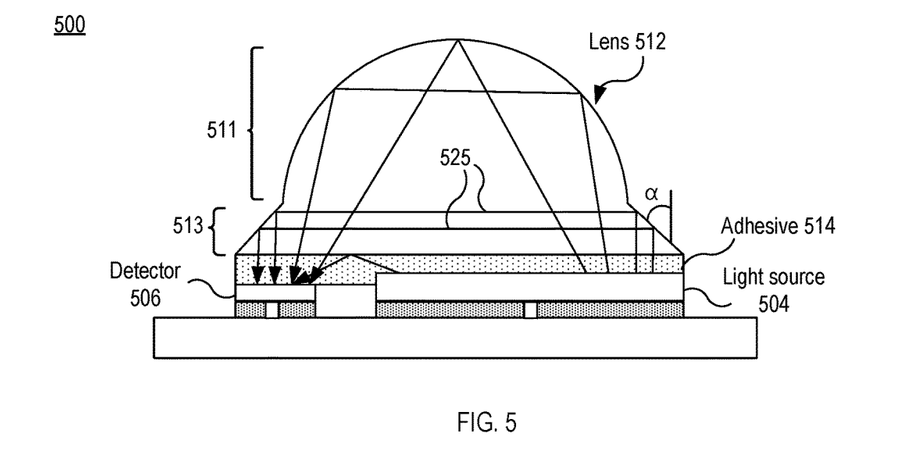
FIG. 5 shows a UV light module according to embodiments of the present invention.

FIG. 5 shows a UV light module 500 according to embodiments of the present invention. As depicted, the UV light module 500 is similar to the UV light module 300, with the difference that the lens 512 has two parts: a spherical dome portion 511 and a conical frustum portion 513. The side wall of the frustum portion 513 may have an inclination angle α such that a portion of the light transmitted through the adhesive layer 514 may be internally reflected on the side wall and transmitted to the detector 506 through the frustum portion 513, as indicated by the arrows 525. As such, the frustum portion 513 may provide a waveguide for transmitting a portion of the light from the light source 504 to the detector 506 therethrough. In one embodiment, the inclination angle α may be about 45 degrees.

Figure 6:
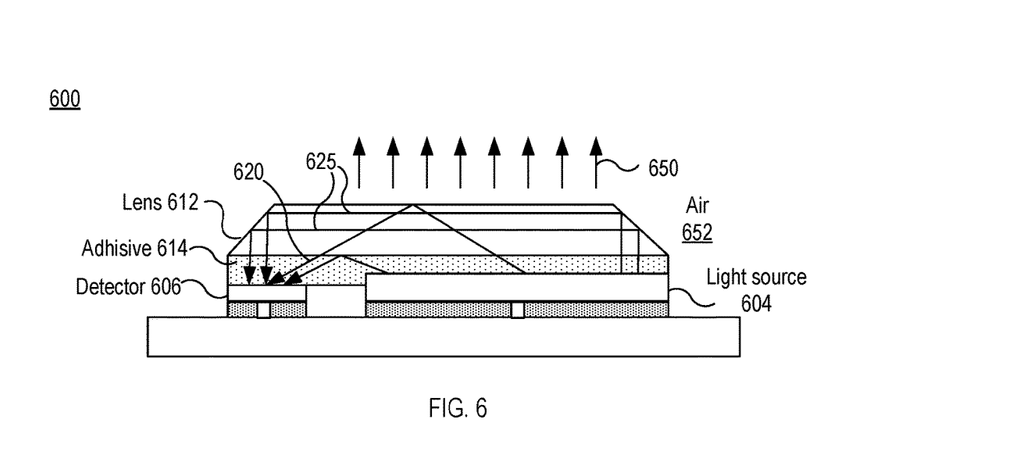
FIG. 6 shows a UV light module according to embodiments of the present invention.

FIG. 6 shows a UV light module 600 according to embodiments of the present invention. As depicted, the UV light module 600 is similar to the UV light module 500, with the difference that the lens 612 has only the conical frustum portion. As in the UV light module 500, the lens 612 may act as a waveguide for transmitting a portion of the light from the light source 604 to the detector 606 therethrough, as indicated by the arrows 625. Also, as in the UV light module 500, the adhesive layer 614 may act as a waveguide for transmitting the light that is internally reflected on the interface between the lens 612 and the adhesive layer 614 therethrough. It is noted that a portion of the output light may be internally reflected on the interface between the lens 612 and the air 652, as indicated by the arrow 620.

It is noted that the lens 612 does not have a spherical dome portion. As such, the light 650 transmitted through the lens 612 may have a uniform two-dimensional distribution over the top surface of the lens 612.

Figure 7:
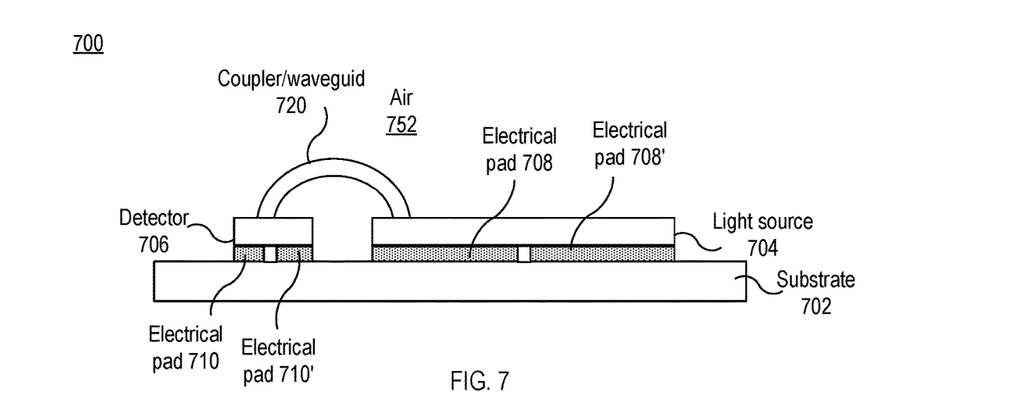
FIG. 7 shows a UV light module according to embodiments of the present invention.

FIG. 7 shows a UV light module 700 according to embodiments of the present invention. As depicted, the UV light module 700 may be similar to the UV light module 100, with the difference that the UV light module 700 does not include a lens and that the UV light module 700 includes a waveguide (or equivalently coupler) 720. The substrate 702, light source 704, detector 706, and electrical pads 708, 708', 710 and 710' may be similar to their counterparts in the UV light module 100, i.e., these components may be formed of similar materials and have similar functions as their counterparts.

In embodiments, the waveguide 720 may have a shape of a tube that has the first end disposed on the top surface of the light source 704 and the second end disposed on the top surface of the detector 706. A portion of the light emitted by the light source 704 may enter the waveguide through the first end, travel through the waveguide 720 by internal reflection on the interface between the waveguide 720 and the air 752, and exit the waveguide through the second end. In embodiments, the waveguide 720 may be formed of material, such as quartz or sapphire that is transparent to the UV light emitted by the light source 704.

The index of refraction of the waveguide 720 may affect the internal reflectance on the surface of the waveguide. As such, the index of refraction of the waveguide 720 may be determined such that the detector 706 can receive sufficient amount of light through the waveguide 720 by the internal reflection on the waveguide surface. Optionally, to increase the reflectance on the interface between the waveguide 720 and the air 752, the outer surface of the waveguide 720 may be coated with light reflecting material, such as aluminum, silver or DBR, to thereby form a light reflecting layer on the surface. Optionally, the area of the first end of waveguide 720 disposed on the top surface of the light source 704 may be adjusted to house enough light transmitted from the light source 704 to the photo detector 706, to guarantee a measurable photocurrent.

In embodiments, the waveguide 720 may be attached to the light source 704 and detector 706 by the attractive Van Der Waal's force, as the lens 112 is attached to the light source 104 and detector 106 in the UV light module 100. In embodiments, the waveguide 720 may be attached to the light source 704 and detector 706 by epoxy or resin that is transparent to the UV light emitted by the light source 704.

Figure 8:
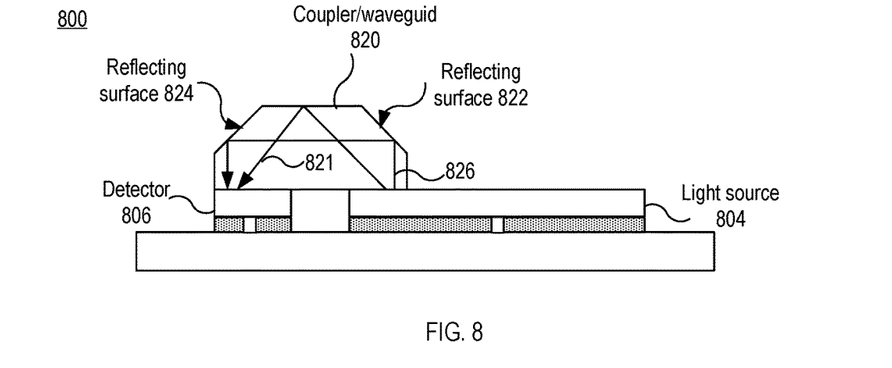
FIG. 8 shows a UV light module according to embodiments of the present invention.

FIG. 8 shows a UV light module 800 according to embodiments of the present invention. As depicted, the UV light module 800 is similar to the UV light module 700, with the difference that the waveguide 820 has a shape of polygonal prism. The waveguide 820 may have at least two reflecting surfaces 822 and 824 on which the light is internally reflected toward the detector 806, as indicated by the arrow 826. In addition, a portion of the light from the light source 804 may be internally reflected on the top surface of the waveguide 820, as indicated by the arrow 821.

In embodiments, the waveguide 820 may be formed of material, such as quartz or sapphire that is transparent to the UV light emitted by the light source 804. The index of refraction of the waveguide 820 may affect the reflectance on the surface of the waveguide. As such, the index of refraction of the waveguide 820 may be determined such that the detector 806 can receive sufficient amount of light through the waveguide 820 by internal reflection on the waveguide surfaces. Optionally, to increase the internal reflectance, the outer surface of the waveguide 820 may be coated with light reflecting material, such as aluminum, silver or DBR, to thereby form a light reflecting layer on the surface.

In embodiments, the waveguide 820 may be attached to the light source 804 and detector 806 by the attractive Van Der Waal's force, as the lens 112 is attached to the light source 104 and detector 106 in the UV light module 100. In embodiments, the waveguide 820 may be attached to the light source 804 and detector 806 by epoxy or resin that is transparent to the UV light emitted by the light source 804.

Figure 9:
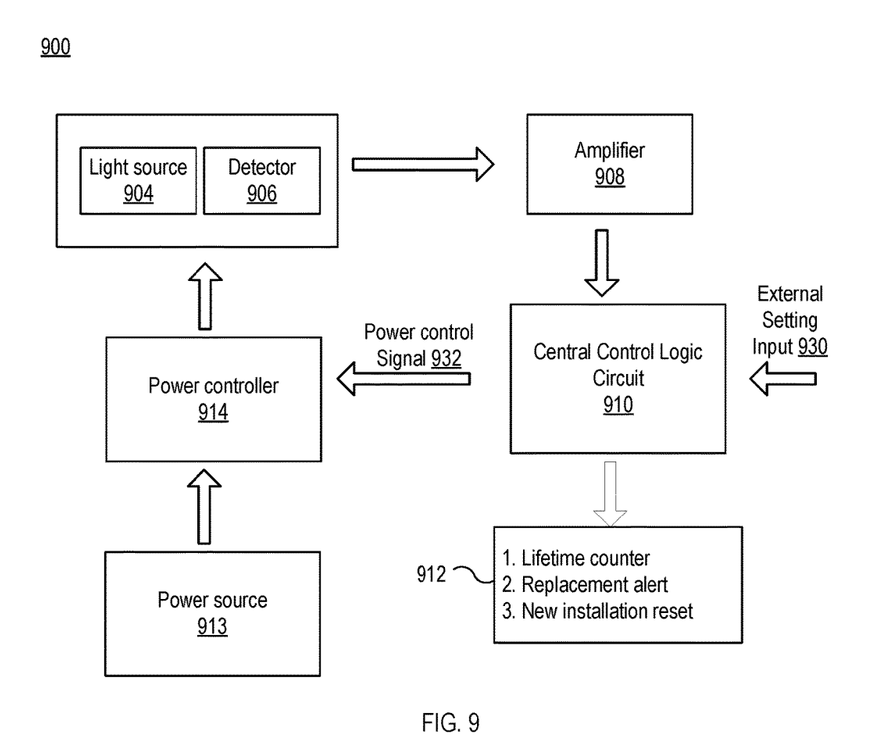
FIG. 9 shows an operational block diagram of a UV light system according to embodiments of the present invention.

FIG. 9 shows an operational block diagram of a UV light system 900 according to embodiments of the present invention. As depicted, the light source 904 (which may be similar to the light sources in FIGS. 1-8) generates UV light and a portion of the UV light is transmitted to the detector 906 (which may be similar to the detectors in FIGS. 1-8). In embodiments, the detector 906 may be a photodiode and generate photocurrent in response to the light incident thereon. In embodiments, the photocurrent may be amplified by the amplifier 908 and sent to the central control logic circuit (or shortly central controller) 910.

A human operator may determine an operational intensity range of the output light generated by the light source 904. Also, assuming that the responsivity of the detector 906 and the gain of the amplifier 908 do not vary in time, the human operator may determine the operational range of the photocurrent from the amplifier 908 based on the operational intensity range of the output light generated by the light source 904. In embodiments, the external setting input 930, which may include the information of the operational range of the photocurrent, may be sent to the central controller 910 via a suitable communication channel. It is noted that the external setting input 930 may include other suitable information/control signal to program the central controller 910.

In embodiments, the central controller 910 may control the light source 904 based on the operational range of the photocurrent. For instance, if the level of the photocurrent signal received from the amplifier 908 is below the operational range, the central controller 910 may send the power control signal 932 to the power controller 914 to increase the current (or power) input to the light source 904. Likewise, if the level of the photocurrent signal received from the amplifier 908 is above the operational range, the central controller 910 may send the power control signal 932 to the power controller 914 to decrease the power input to the light source 904. Thus, the amplifier 908, central controller 910, and power controller 914 may form a feedback mechanism/loop for controlling the intensity of light emitted by the light source 904. Hereinafter, the term feedback loop collectively refers to one or more components that participate in controlling the input current (or input power) to the light source 904 based on the output signal from the detector 906.

In embodiments, the power controller 914 may receive electrical power from the power source 913 through a wires and adjust the power (or current) input to the light source 904 according to the power control signal 932 received from the central controller 910.

In embodiments, the central controller 910 may send additional output signals to an external device(s) via a suitable communication channel, such as the wire, to thereby perform the extended functions 912. For instance, the light source 904 may be an UV light emitting diode (LED) and its output intensity may slowly decrease over time in a process, known as lumen depreciation. To monitor the operational lifetime of the light source 904, the central controller 910 may send control signals to a lifetime counter on a regular basis. In another example, the central controller 910 may send a replacement alert when it determines that the intensity of the output light from the light source 904 cannot be controlled by the feedback loop and the light source 904 needs to be replaced. In yet another example, the central controller 910 may send a reset signal when one of the components in the UV light system 900 is replaced and a new installation reset is needed. It is noted that the extended functions 912 does not show an exhaust list of functions to be performed by the central controller 910 for proper operation of the UV light system 900.

It is noted that one or more of the components in the UV light system 900 may be mounted on (or embedded in) a substrate (which is similar to the substrates in FIGS. 1-8). For instance, the central controller 910 may be a chip that may be mounted on the substrate. In another example, the amplifier 908 may be a circuit embedded in a PCB substrate.

It is also noted that one or more of the components in the UV light system 900 may be optional. For instance, the amplifier 908 may be omitted if the photocurrent from the detector 906 is high enough to be processed by the central controller 910 without amplification. It is further noted that one or more of the components in the UV light system 900 may be combined into one component and/or one of the components in the UV light system 900 may be implemented as multiple components.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. An apparatus for generating light, comprising:
    a substrate;
    a light source mounted on a top surface of the substrate, the light source generates output light;
    a detector mounted on the top surface of the substrate, the detector detects light incident thereon; and
    a waveguide consisting of a single body having a shape of a polygonal prism, a base of the polygonal prism consists of five sides so that the polygonal prism has five flat side surfaces, one of the five flat side surfaces including a first portion that is in direct contact with the light source and a second portion that is in direct contact with the detector, wherein a portion of the output light enters the waveguide through the first portion, travels through the waveguide and exits the waveguide through the second portion to the detector, wherein the light source includes a top surface and emits the output light through the top surface and wherein a surface area of the light source where the first portion of the one of the five flat side surfaces directly contacts the top surface of the light source is less than an entire area of the top surface of the light source.

2. The apparatus as recited in claim 1, further comprising:
    a feedback loop that controls a power input to the light source using an output signal from the detector.

3. The apparatus as recited in claim 2, wherein the feedback loop includes:
    a central controller responsive to the output signal from the detector and operative to generate a control signal for controlling the power input to the light source.

4. The apparatus as recited in claim 3, wherein the feedback loop includes:
    a power controller responsive to the control signal from the central controller and operative to adjust the power input to the light source.

5. The apparatus as recited in claim 1, wherein the light source is secured to the substrate by one or more electrical pads.

6. The apparatus as recited in claim 1, wherein the detector is secured to the substrate by one or more electrical pads.

7. The apparatus as recited in claim 1, further comprising:
    a light reflecting layer disposed on a surface of the waveguide.

8. The apparatus as recited in claim 1, wherein the substrate includes a printed circuit board (PCB).

* * * * *